United States Patent
Brasilino de Carvalho et al.

(10) Patent No.: US 8,372,791 B2
(45) Date of Patent: Feb. 12, 2013

(54) COSMETIC COMPOSITION FOR SKIN CLEANSING

(75) Inventors: André Luís Brasilino de Carvalho, São Bernardo do Campo (BR); Rodrigo Pereira Lima, Jundiaí (BR); Juliana Bucchi Alencastre, Osasco (BR); Viviane Cristine Boschetti, São José dos Campos (BR); Elisangela De Souza Costa, São Paulo (BR); Reinaldo Rubens Miguel, Jundiaí (BR); Janaina Ferreira Alves, São Paulo (BA)

(73) Assignee: Natura Cosmeticos S.A., Itapecerica da Serra—SP (BR)

( * ) Notice: Subject to any disclaimer, the term of this patent is extended or adjusted under 35 U.S.C. 154(b) by 5 days.

(21) Appl. No.: 13/129,952

(22) PCT Filed: Nov. 23, 2009

(86) PCT No.: PCT/IB2009/007545
§ 371 (c)(1),
(2), (4) Date: Aug. 4, 2011

(87) PCT Pub. No.: WO2010/058287
PCT Pub. Date: May 27, 2010

(65) Prior Publication Data
US 2011/0294711 A1    Dec. 1, 2011

(30) Foreign Application Priority Data

Nov. 18, 2008 (FR) .................................. 08 57825

(51) Int. Cl.
*A61K 8/00* (2006.01)
(52) U.S. Cl. ........ 510/130; 510/141; 510/152; 510/155; 510/462; 510/463
(58) Field of Classification Search ........................ None
See application file for complete search history.

(56) References Cited

U.S. PATENT DOCUMENTS

| 5,801,134 A | 9/1998 | Righton |
| 2008/0015271 A1* | 1/2008 | Abram et al. ................... 521/94 |

FOREIGN PATENT DOCUMENTS

| FR | 2 779 648 A1 | 12/1999 |
| GB | 356847 | 9/1931 |
| WO | WO 98/18896 | 5/1998 |
| WO | WO 2004/022684 A1 | 3/2004 |

OTHER PUBLICATIONS

Search Report for International Application No. PCT/IB2009/007545, mailed Jan. 19, 2011.
Preliminary Report on Patentability for International Application No. PCT/IB2009/007545, issued May 24, 2011.

* cited by examiner

*Primary Examiner* — Necholus Ogden, Jr.
(74) *Attorney, Agent, or Firm* — Alston & Bird LLP

(57) ABSTRACT

The present invention describes a cosmetic composition for skin cleansing, the end product of which has peculiar and improved physical characteristics with regard to plasticity, malleability, moldability and non-friability. Said peculiar and improved physical characteristics occur because of the presence of a structural analog of vegetable starch in the formulation of the end product. Said cosmetic composition for skin cleansing comprises: at least one surfactant; fecula; at least one cosmetic agent and a cosmetically acceptable carrier.

17 Claims, 4 Drawing Sheets

COSMETIC COMPOSITION FOR SKIN CLEANSING

FIELD OF THE INVENTION

The present invention relates to a cosmetic composition for skin cleansing.

Said composition has innovative and improved physical features with regard to malleability, plasticity, moldability and non-friability of the end product.

DESCRIPTION OF THE PRIOR ART

The medical use of soaps leads to records mentioning their medicinal and cleansing properties. Some scholars have used soap to try to solve several skin problems, including scabies, psoriasis, ringworm, tinea versicolor and *Herpes tonsurans*. In Europe, in the nineteenth century, treatments were described with the use of versicolor soap for acne vulgaris and mycosis. In the United States, the possibility of treating acne with a fine soap of olive oil and caustic soda had been assessed.

In general, soaps are made from the chemical reaction between fat and an alkali, resulting in a fatty acid salt with detergent action. Soaps using colors and aromas were first developed in France.

In the 1950s, with the development of the chemical industry and the improvement of formulas, there were lower levels of allergies associated with the use of soaps as well as a reduction in their cost. The soapmaking technology has greatly evolved in the last years and these products have gained other roles, such as moisturizing and protection, but eliminating dirt, dead cells, excessive oil and sweat produced by glands is still the basic function of every soap bar.

With time, the chemical industry developed soaps that are less aggressive to the skin, such as glycerin soaps, for instance. Other industries have also helped this development, creating equipment that rendered large-scale soap manufacturing quicker and more efficient.

Several components of plant, animal and/or mineral origin can be incorporated into the composition of soaps, such as oils, fatty acids, emulsifying esters, surfactant molecules, foaming agents, fragrances, vegetable polysaccharides, extracts, whole parts of plants (exfoliation), among others.

Polysaccharides or glucans are carbohydrates which generate several monosaccharides by hydrolysis. They are natural polymers. For instance, cellulose is a glucose polymer:

$n\text{glucose} \rightarrow \text{Cellulose} + n\text{H}_2\text{O}$

Polysaccharides are then macromolecules formed by joining several monosaccharides. These compounds have a very high molecular mass, which depends on the number of monosaccharide units that are joined. They can be hydrolyzed into smaller polysaccharides, as well as in disaccharides or monosaccharides with the action of certain enzymes.

In the living organisms, polysaccharides are classified into two groups depending on their biological function:
  Energy reserve polysaccharides: the energy-providing molecule for living beings is mainly glucose. When it is not part of the energetic metabolism, it is stored in the form of a polysaccharide, which in the plants is known as starch and in the animals is known as glycogen.
  Structural polysaccharides: these carbohydrates participate in the formation of organic structures, cellulose being the most important one, being the structural component of plants.

Polysaccharides have the following general formula:

$-[C_x(H_2O)_y)]_n-$ wherein y is generally x−1. (Source: "http://pt.wikipedia.org/wiki/Polissacar%C3%ADdeo")

Finally, polysaccharides can also be classified according to their solubility in water. (Rombi, 1991; Bruneton, 1993; Spiller, 1994).

Starch is synthesized in plant structures called plastids: chromoplasts of the leaves and amyloplasts of storage organs from the polymerization of glucose resulting from photosynthesis.

In plants, the glucose polymer used as storage is starch, which has a very similar structure to that of glycogen, but is less branched than glycogen.

Starch has been used by men since ancient times. The Chinese and Egyptians were the first to know about this substance. The Greek differentiated it from wheat calling it amylum.

Currently, "starch" is normally used to designate the amylaceous substance extracted from fruits and seeds, and "fecula" is used to designate any pulverulent farinaceous matter, extracted from tubers and roots and processed from starchy grains, such as: manioc (or cassava) fecula.

In general, starch and its analogs can be divided into two large groups: fecula, which is an amylaceous fraction of underground raw material; and starch, which is more "general", obtained from the upper parts of plants, and from cereals, legumes and others. Examples: wheat starch, rice starch, corn starch, manioc fecula, potato fecula.

Although this type of substance is very frequent in the vegetable kingdom, there are relatively few plants used for obtaining it in large scale.

Starch or fecula are always whitish, fine powders, formed by granules of variable size, shape and layers.

The cosmetic use of vegetable starches, more specifically, their use in cleansing compositions and in the conditioning of keratin materials is known in the prior art.

Patent document US 2005/069511 discloses a soap composition having as components at least one starch and at least one ester. Said composition free of soap and can be easily rinsed off, and has a melting texture.

Document MXPA06013378 discloses a liquid cleansing composition comprising water-soluble or water-swellable starch that when combined with linear C-8 to C-13 fatty acid form a structural network which prevent phase separation.

Korean document KR 20010076246 relates to a cosmetic composition comprising amphoteric starch and cationic conditioner, as quaternary ammonium salts, cationic silicones, among others. This composition has improved cosmetic properties such as smoothness, lightness, and suppleness and is used for skin and/or hair cleansing.

Mexican document MX 9708983 discloses solid products whose matrix consists of an alveolar network formed from a starch-rich product and contains at least one polymeric or copolymeric expanded thermoplastic hollow particle of an ethylenically unsaturated monomers mixture or monomeric mixtures. This composition can be rehydrated for use and presents galenic forms of skin cleansing products.

Korean document KR 20010076245 relates to a cosmetic composition for skin cleansing and conditioning. This composition comprises in a washing base at least one specific amphoteric starch. The composition described in the Korean application does not contain fatty acid salts.

European document EP 1496844 discloses cosmetic and dermatological cleansing preparations comprising one or more pregelatinized, cross-linked starch derivatives, and; one or more ethoxylated oils.

These known cosmetic compositions use vegetable starches as binders and do not have differentiated physical characteristics.

The prior art also describes skin cleansing compositions having particular physical characteristics such as plasticity and viscosity.

U.S. Pat. No. 5,801,134 relates to a non-hardenable cleansing product for personal use having a plasticine-like consistency. Said composition comprises 35% to 80% by weight of powder material, such as Kaolin, silicates, starches, among others; 10% to 25% by weight of surfactant material and 5% to 28% by weight of anhydrous base material to give a pH neutral product.

U.S. Pat. No. 5,948,395 describes an anhydrous cosmetic composition in the form of a soft paste, which during its preparation is kneaded, thus resulting in said paste having a differentiated consistency.

U.S. Pat. No. 6,300,297 relates to a soap composition having starch as one of its components. Said composition, when applied to cosmetic bases, confers the end product relative rheology, non-hygroscopy and break resistance.

From the description of the present invention provided below, it can be concluded that no prior-art teachings describe the use of fecula as a binding agent promoting malleability, moldability, plasticity and non-friability for a cosmetic product such as, for instance, a soap. Fecula, as may be seen below, when combined with other chemical components specified herein, exhibits some superior characteristics over starch, resulting in products with improved attributes.

OBJECTS OF THE INVENTION

The object of the present invention is to provide a cosmetic composition for skin cleansing, the end product of which exhibits plasticity, malleability, moldability and non-friability characteristics because of the presence of fecula in its formulation.

BRIEF DESCRIPTION OF THE INVENTION

The present invention relates to a cosmetic composition for skin cleansing used in the form of a solid composition having malleability and plasticity characteristics when dried or wet, comprising:
 a) From 1% to 45% by weight of at least one surfactant;
 b) about 36% by weight of fecula;
 c) from 0.03% to 4% by weight of a cosmetically acceptable carrier;
 d) from 15% to 63% by weight of at least one cosmetic agent;
 wherein all amounts refer to the total weight of the composition.

In one embodiment, the present invention is directed to a non-hardenable cosmetic composition for skin cleansing used in the form of a solid composition having malleability and plasticity characteristics when dried or wet, comprising:
 a) from 1% to 54% by weight of at least one surfactant;
 b) about 36% by weight of fecula;
 c) from 0.03% to 4% by weight of a cosmetically acceptable carrier; and
 d) from 8% to 63% by weight of a cosmetic agent; wherein all amounts refer to the total weight of the composition.

DETAILED DESCRIPTION OF THE INVENTION

The present invention describes a cosmetic composition for skin cleansing, the end product of which has peculiar and improved physical characteristics with regard to plasticity, malleability, moldability and non-friability.

Said peculiar and improved physical characteristics occur because of the presence of fecula in the formulation of the end product combined with other chemical components that will be further described.

Said fecula has the function of a binding agent (binder) and/or a malleability agent in the formulation. This component is selected from the group of vegetable and/or synthetic types of fecula.

One of the preferred embodiments of the invention is a malleable soap, that is, it is a cosmetic composition for skin cleansing having a consistency that is similar to that of play dough. It is a galenic form of soap between the liquid soap and the soap bar.

Most of the known formulations disclosed for soaps having differentiated/unusual physical characteristics show some drawbacks with regard to the practical and pleasant use of the end product.

The present cosmetic composition for skin cleansing is advantageous over other known, malleable cosmetic compositions, because:
 it is not friable;
 it is not slippery,
 it does not leave product residues on the user's skin (specially in the hands), and
 it is extremely malleable and moldable, acquiring the shape desired by the user.

The present composition has other suitable and safe physical-chemical characteristics for the end user:
1. It is stable for a period of at least two years, provided it is duly kept in its original package;
2. It keeps a suitable texture during application, which is non-sticky and non-oily;
3. It slides easily;
4. It does no cause skin oiliness after application;
5. It is non-comedogenic;
6. It is not phototoxic;
7. It is not allergenic;
8. It does not cause adverse reactions or skin or eye damage, either in conditions of normal use or forced sweating;
9. As it does not cause skin irritation, it is more comfortable and can be used daily or even more than once a day;
10. It has proper chemical stability;
11. It has suitable malleability and moldability achieving the object of the present invention;

12. It is ideal for children, since it is a playful cleansing product.

Cosmetic Composition for Skin Cleansing

The cosmetic composition for skin cleansing of the present invention comprises at least one surface active agent (surfactant) in an amount that ranges between 1% and 45% by weight; fecula at about 36% by weight; and at least one cosmetically acceptable carrier ranging between 0.03% and 4% by weight, from 15% to 63% by weight of at least one cosmetic agent, all quantities above being based on the total weight of the composition.

Surface Active Agent:

The surface active agents, also called surfactants, are substances that reduce the surface tension or influence the contact surface between two liquids. When used in domestic technology, they are generally called emulgents, that is, substances that enable one to achieve or maintain the emulsion state.

The compounds are based on molecules in which one of the parts is water-soluble and the other is fat soluble (has higher affinity for fats and other apolar substances).

Surface active agents can be classified as:

Cationic surfactants: The cationic surfactants are characterized by having a positively charged hydrophilic group linked to the hydrophobic fatty chain.

Some important properties of said surfactants make them suitable for use in cosmetic preparations such as bactericides and anti-static agents in hair conditioners.

The cationic surfactants that are most used in cosmetic preparations are the quaternary ammonium salts and, among them, cetyltrimethylammonium chloride, but dialkyldimethylammonium chlorides are also widely used.

Anionic surfactants: The anionic surfactants, when in aqueous solution, have a negative charge in their hydrophilic portion. The main representatives of this class are the fatty acid soaps, the alkyl sulfates, the alkyl ether sulfates and the alkyl sulphosuccinates, although several others are also important for one or another specific use. As a rule, they have high foaming power, high detergency level and high humectation when compared to the other surfactant classes.

The fatty acid alkaline soaps are used in the manufacture of soap bars because their performance is satisfactory and their cost is low. Normally, the anionic surfactants produce less foam and are more susceptible to water hardness. The addition of chelating and scavenging agents can improve the performance of said products.

The alkyl sulfates in addition to the alkyl ether sulfates are most used as foaming surfactants in hair cosmetics, liquid soaps, oral hygiene products, among other applications. The most important alkyl sulfates are the lauryl sulfates which have a broad application in cosmetics. The main characteristics of the alkyl sulfates are: high foaming power, high viscosity reserve, good water solubility, pleasant odor and complete biodegradability.

The most important alkyl ether sulfates are the lauryl ether sulfates, because of their differentiated properties. They are more hydrophilic (50%) than their non-ethoxylated counterparts; they cause low eye and skin irritation, low turbidity, easy viscosity control from the addition of electrolytes and greater water hardness resistance.

Additionally, the alkyl sulphosuccinates are also anionic surfactants, which have excellent moisturizing power although they produce little foam and have low detergency power. The monoalkyl sulphosuccinates were recently developed, and they are slightly irritating to the eyes and have very low toxicity.

The alpha-olefin sulphonates, the taurates and sarcosinates are also anionic surfactants of low irritability, but contrary to the sulphosuccinates, they are rich in foam.

Amphoteric surfactants: The amphoteric surfactants are characterized by presenting positive and negative groups in the same molecule. The positive group is generally represented by a quaternary nitrogen group and the negative is represented by a carboxylate or sulphonate group.

Properties such as solubility, detergency, foaming power and moisturizing power of this class of surfactants are mainly dependent on the pH of the medium and the length of the chain that constitutes them. The positive polar group is stronger with a pH value of less than 7, while the negative polar group is stronger with a pH value greater than 7. The most used amphoteric surfactants in the cosmetic industry are the imidazoline and the betaine derivatives.

Nonionic surfactants: The nonionic surfactants are characterized by having neutral hydrophilic groups linked to the fatty chain. Their characteristics include: compatibility with most raw materials used in cosmetics, low eye and skin irritation, high level of surface and interfacial tension reduction and low detergency and foaming power. These characteristics enable these surfactants to be used mainly as emulsifying agents.

The fatty acid alkanolamides belong to the class of nonionic surfactants.

Among the nonionic surfactants, the fatty alkanolamides are most used in foamy preparations, specially in shampoos, because they have a thickening power by increasing the viscosity reserve, that is, because they enable higher water absorption and greater resistance to electrolytes, foam stabilization by the solubilization of fatty esters, glycols, alcohols, essential oils, lanolin, etc., superfatting effect (reconditioning) due to the fatty structure and low detergency power, and they reduce the drying effect caused by anionic surfactants.

Other components of the nonionic class of surfactants are the polyol derivatives, such as glycerol esters. Among them, the glyceryl monostearate is the most used in lotions, creams and lipsticks.

Among the polyols, there is still the class of glycol derivatives, in which the glycol esters are the simplest components.

Several nonionic surfactants are also used as emollients acting in the prevention and relief of dry skin as well as its protection. These substances provide smoothness and flexibility to the skin. They act retaining water in the stratum corneum by forming a water-in-oil emulsion. The emollient nonionic surfactants also have the following properties: easy spreading, easy skin penetration, they help in pigment dispersion, they act as emulsifying agents and co-solvents. An example of this product category is propoxylated stearyl alcohol, which is widely used in this function because it is not comedogenic (acne causing).

Nonionic surfactants can also be used as consistency agents, including ethoxylated ketostearyl alcohol with 20 mols of ethene oxide, normally used together with the starting material for its synthesis (non-ethoxylated ketostearyl alcohol) in hair conditioners and several creams.

The alkylpolyglucosides are a relatively new family of surfactants. They are good detergents and have a very high degree of biodegradability. The main surfactants of this class are decyl and laurylpolyglycoside with a polymerization degree (average number of glucose units per alcohol unit) of 1.4.

Preferably, the surface active agent of the present cosmetic composition for skin cleansing is selected from the group consisting of: sodium palmate, sodium palm kernelate, sodium stearate, glycerin, cocamidopropylbetaine, decyl-glucose, sodium tridecyl sulphate.

In the preferred embodiments, the surfactant is selected from sodium palmate, sodium palm kernelate, sodium stearate, glycerin, cocamidopropylbetaine, decyl-glucose, sodium tridecyl sulphate, sodium lauryl sulphate, sodium lauryl ether sulphate, cupuacuamidopropryl betaine, preferably sodium palmate, sodium palm kernelate, sodium stearate, glycerin, sodium tridecyl sulphate in an amount varying from 1% to 45%, preferably from 4.5% to 38.6% by weight based on the total weight of the composition.

Fecula

Fecula acts in the cosmetic composition of the present invention as a binding agent and/or malleability agent.

Currently, "starch" normally is used to designate the amylaceous substance extracted from fruits and seeds, and "fecula" is used to designate any pulverulent farinaceous matter, extracted from tubers and roots and processed from starchy grains, such as: manioc (or cassava) fecula.

In general, starch and analogs can be divided into two large groups: fecula, which is an amylaceous fraction of underground raw material; and starch, which is more "general", obtained from the upper parts of plants, and from cereals, legumes and others. Examples: wheat starch, rice starch, corn starch, manioc fecula, potato fecula.

Starch or fecula are always whitish, fine powders, formed by granules of variable size, shape and layers.

The microscopic observation of a starch grain can reveal the presence of a point or a groove, which can be simple or crossed, centric or eccentric, such formations being called hilum.

Around the hilum there may or may not be a succession of light and dark zones, which are called lamellae, striae or layers.

The position and the shape of the hilum are important in the identification of the starch grain, as well as the centricity of the lamellae.

The shape, structure and type of hilum, the aggregation state are important features in the identification of starches and fecula.

According to said features, the starch grains can be classified as follows:
i) With Regard to Shape
a) Spherical
b) Ovoid
c) Polyhedral
d) Dome-shaped
e) Reniform
f) Dumbbell-shaped
ii) With Regard to Structure
a) Homogeneous
b) Stratified
iii) with Regard to the Type of Hilum
a) Punctiform
b) Linear
c) Cruciform
d) Star-shaped
e) Circular
f) Polyhedral
iv) With Regard to the Aggregation State
a) Simple or isolated
b) Compound
b.1) Grouped, aggregated or compound itself;
b.2) Pseudo-compound.

Common Types of Starches and Fecula:

Wheat Starch (*Triticum vulgare* VII):

The wheat starch grains are lenticular when seen from the front or biconvex when seen from the side. They have concentric striation that is not very visible and a spotted hilum in rare grains. The smaller grains have a globular or slightly polygonal shape. On average, they have 20 to 30 μm diameter and can reach a diameter of up to 40 μm. In the polarized light, the "cross" is not very clear.

Corn Starch (*Zea mays* L.):

It is most used in the preparation of sweets, creams and cakes and, for this reason, it is industrially manufactured in large scale. The grains are quite polyhedral when they come from the external part of the seed and their sides are slightly bulged. The grains of the central white zone are almost spherical and much smaller. The hilum is spotted, having short, star-shaped prolongations.

The striae are rarely visible and they are not grouped into compound grains. In general, they measure 30 μm. In the polarized light, they have a very visible "cross", either in the dark or in the light field.

Manioc Fecula (*Manihot esculenta* Grantz):

Also known as "Brazilian arrowroot." The fecula grains are spherical or irregularly rounded and thimble-shaped, having truncated spheres in one or more facets and they vary from 25 to 35 μm in diameter. Linear or star-shaped spotted hilum, generally, the center of the grain. Both the small and the large grains have been aggregated from 2 to 3 elements. Striae are not quite visible. The starch "cross" is perfectly noticed.

The composition of the present invention contains fecula and, for this reason, it has improved plasticity, moldability, malleability, "non-friability" characteristics in comparison with the known compositions that contain vegetable starch. The improved characteristics are basically due to the structure of the fecula (shape and dimensions). This structure, when combined with other chemical components specified herein result in a composition having singular attributes and features.

The fecula grains have a spatial structure that is more favorable to grain compression and thus to the increased malleability of the formulation of the invention.

In the preferred embodiments, fecula selected from vegetable or synthetic fecula is added, preferably manioc fecula in an amount that varies around 36% by weight, based on the total weight of the composition.

Carrier

Water is the basis of various embodiments of the cosmetic composition of the present invention, acting as a carrier for the other components. The compositions of the present invention comprise preferably demineralized or distilled water at a suitable percentage (q.s.p.) to solubilize the ingredients of the formulation (e.g., dyes). Naturally, other cosmetically acceptable carriers may be used in the present invention.

Cosmetic Agents:

Some non-exhaustive examples of cosmetic agents that are compatible with the composition properties described herein will be provided below. They can be used in the present cosmetic composition for skin cleansing:

Antioxidant agents: BHT, tocopherol and/or derivatives thereof, catechins, tannins and/or derivatives thereof, phenolic compounds, hydroquinone, among others;

Preservative agents: methyl parabens, propyl parabens, isothiazolinonic, phenoxyethanol;

Film-forming agents: agar gum, carrageenan gum, alignates, gum arabic, gelatin;

Microcrystalline support network forming agents: dextrans, methyl-acrylates, PHB, PHA;

Polymeric and/or copolymeric agents: silicone copolymers, siloxane and/or modified silicone polymers, acrylate copolymers;

Denaturating agents: denatonium benzoate;

Consistency agents: vegetable wax, mineral hydrocarbons, paraffin, bee wax, white wax, cocoa butter, shea butter, sugarcane wax;

Emollients: liquid paraffin, palm oil, cupuacu butter, lecithin, milk amino acids, wheat protein, vegetable proteins, phospholipid vegetable oils, ceramides, passion fruit ceramide, sphingolipids, whale spermacete, lanolin, almond oil, dicapryl carbonate, silicone elastomers, cyclomethicone;

Humectant and/or moisturizing agents: glycerin, propylene glycol, hyaluronic acid, urea, PCA;

Conditioning agents: quaternary ammonium salts, silicones, siloxanes.

ILLUSTRATIVE EXAMPLES OF COMPOSITIONS ACCORDING TO THE PRESENT INVENçÃO

The examples below are preferred embodiments of compositions for skin cleansing having peculiar and improved physical characteristics and should not be interpreted as limitations thereof. In this sense, it is to be understood that the scope of the present invention encompasses other possible embodiments and is limited only by the content of the appended claims, including therein the possible equivalents.

Example 1

Malleable/Moldable Soap Mass

| Components | % | Function |
|---|---|---|
| Sodium palmate, sodium palm kernelate, sodium stearate, glycerin | 38.5405 | Surface active agent |
| Lecithin | 3.0000 | Emollient |
| Cocoa butter | 4.0000 | Consistency agent |
| Cocamidopropyl betaine | 5.0000 | Surfactant |
| *Manioc fecula* | 35.8595 | Binder/Malleability agent |
| Capric/caprylic triglyceride | 1.0000 | Film-forming agent |
| Decyl-glucose | 6.0000 | Surfactant |
| Sodium trideceth sulfate | 4.5000 | Surfactant |
| Methylchloroisothiazolinone/ methylisothiazolinone | 0.0300 | Preservative |
| BHT | 0.0500 | Antioxidant |
| Denatonium benzoate | 0.0100 | Denaturating agent |
| Water | 1.0000 | Carrier |

Figure 5:
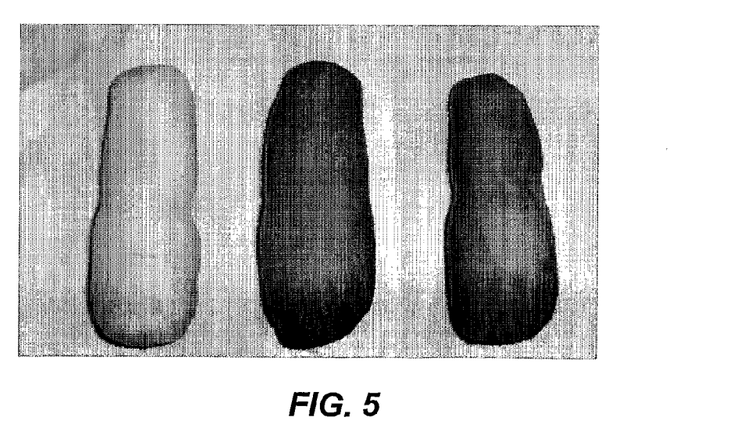
FIG. 5 is a picture illustrating in a non-restrictive way the texture and malleability of the end product.

FIG. 5 illustrates a preferred mode of the product exemplified above.

In other embodiments, the cosmetic composition of the present invention can assume other shapes, since it is malleable and moldable, and can also have other colors.

It can also be presented to the consumer in variable shapes and designs in order to provide different usage possibilities, and fun.

Affective Sensory Test/Study:

Objective of the test: To identify sensory differences between the cosmetic composition for skin cleansing of the present invention and a reference soap prototype having differentiated textures. Example 1 describes the tested composition.

Sample profile: 36 volunteers with 18 years old or more participated in the study.

Figure 1:
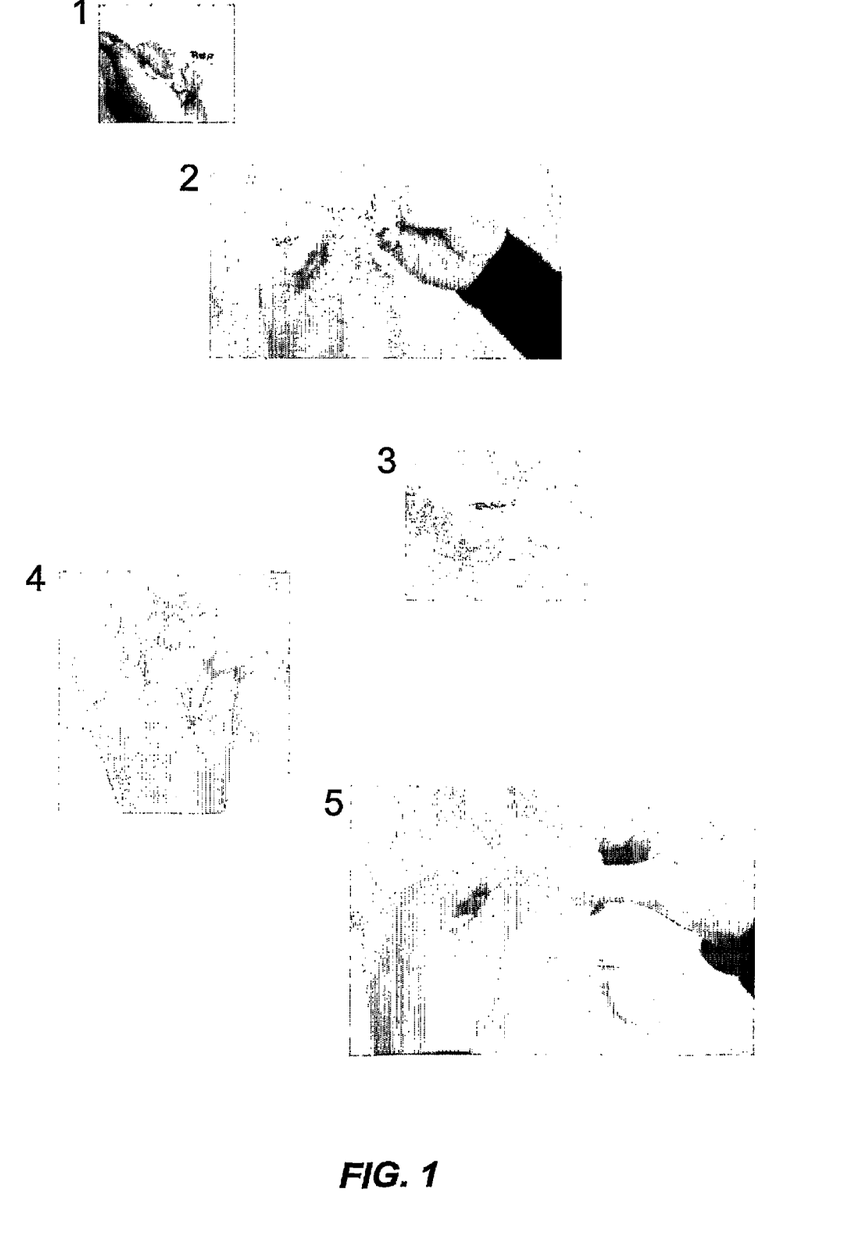
FIG. 1 depicts the attributes assessed in the affective sensory test.

Study Methodology:

i) The samples were coded with three digits, kept in standardized packages and randomly presented;

ii) Each volunteer assessed all the samples in a 10 cm analog scale, according to the following attributes: hardness/firmness, ease of breaking; global appearance after breaking; malleability; stickiness, moldability, all the attributes being illustrated in FIG. 1;

iii) The assessment was carried out in triplicate;

iv) The statistical analyses performed were: ANOVA (Univariate Analysis of Variance), Tukey's test and GPA (Multivariate—Generalized Procrustes Analysis), with confidence level of 95%;

v) XLSTAT 2007 was the statistical software used in the analyses.

TABLE 1 shows the attributes and the methodology of the analysis:

| Attribute | Definition | Methodology |
|---|---|---|
| 1 - Hardness/ Firmness | Soap mass resistance when squeezed between the hands | Hold the mass in one of the hands. Opening and closing the hands, squeeze it between the fingers. Check the hardness of the mass. |
| 2 - Ease of breaking | How easy it is to separate the soap mass in two parts | Roll the soap mass. Break it in two parts and check how easy it is to break the mass. |
| 3 - Smooth appearance of the cross section after breaking | After breaking in two parts, how smooth is the section. | Roll the soap mass. Break in two parts. Check the appearance of the cross section. Not very smooth: presence of irregularities. Very smooth: absence of irregularities. |
| 4 - Malleability | How easy it is to change the shape of the mass and to squeeze it between the fingers. | Make a "ball" with the soap mass. Press the center of the mass with the tip of the fingers. |
| Stickiness | Amount of soap mass that adheres/sticks to the hands and fingers. | Take the sample of the soap mass. Make a "ball" and determine the amount of mass residue that adheres to the hands and fingers. |
| 6 - Moldability | How easy it is to mold the mass in a rounded/flat shape | Take the sample of the soap mass. Make a "ball" and mold it with the fingers in a round/flat shape. Assess how easy it is to mold the mass. |

Figure 2:
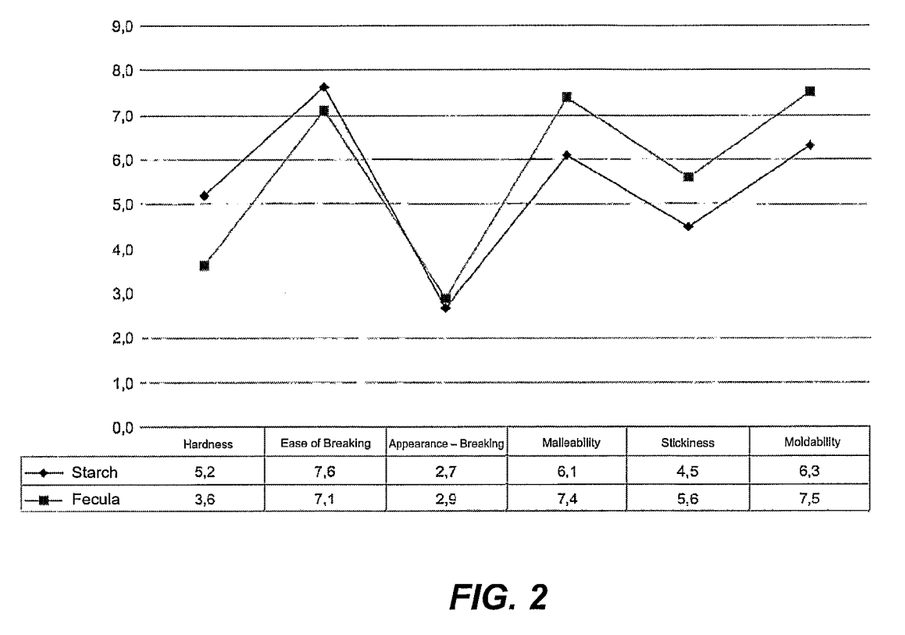
FIG. 2 shows the resulting chart from the assessment of sample discrimination in the sensory evaluation panel—Sensory Profile.
Figure 3:
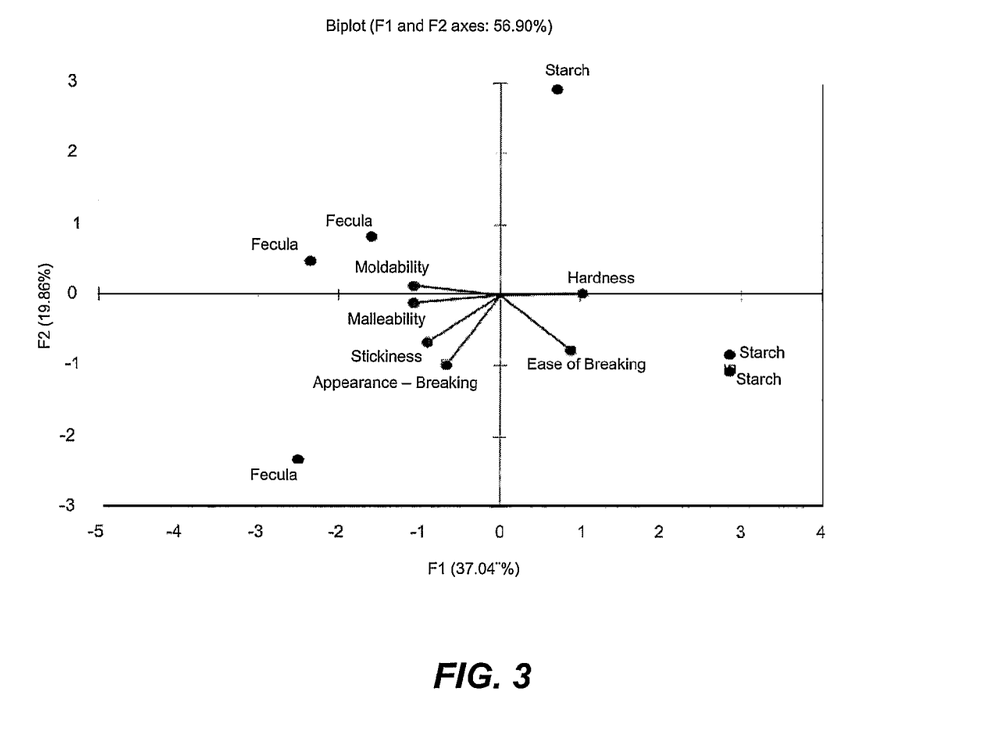
FIG. 3 shows the resulting chart from the assessment of sample discrimination in the sensory evaluation panel—Free Profile.

Assessed samples:

Formula (A)—composition developed based on U.S. Pat. No. 5,801,134 containing starch;

Formula (B)—composition of example 1;

Results of the assessments:

The results of the above described evaluation are detailed in the graphs illustrated in FIGS. 2 and 3, respectively.

Still concerning the graph illustrated in FIG. 3, each product is next to the attribute (vector) that characterizes it, and products with similar characteristics are close to each other. The Procrustes analysis is intended to map the samples according to the attributes of interest through the configuration of the consensus matrix between the evaluators. Once again, it is noted that the evaluators perceived the products differently, which was proven by the means test (Tukey) with a confidence level of 95%.

Based on the results obtained in this sensory evaluation test/study, the existence of significant sensory differences ($p<0.05$) is confirmed between the samples containing vegetable fecula and vegetable starch.

Thus, it is proven that the cosmetic composition of the invention has improved attributes of less hardness, and higher stickiness, malleability and moldability than those achieved with starch, which is used in prior-art compositions.

The composition containing starch was shown to be friable, not sticky and hard/firm. The composition containing fecula overcame said drawbacks being also less hard and consequently more malleable and moldable, being more sticky.

Figure 4:
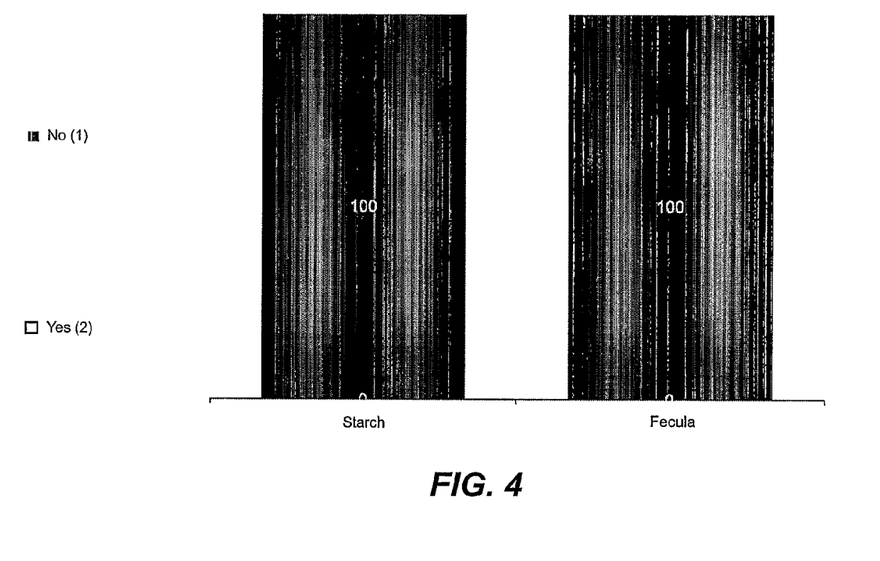
FIG. 4 shows the resulting chart from the adverse reaction test carried out comparing a sample containing vegetable starch and a sample containing vegetable fecula.

Furthermore, a test was conducted with 79 volunteers to check possible adverse reactions. No volunteer showed any problems with the use of the product. The results obtained are shown in FIG. 4.

The invention claimed is:

1. A composition for skin cleansing used in the form of a solid composition having malleability and plasticity characteristics when dried or wet, comprising at least one surfactant, a cosmetically acceptable carrier, and about 36% by weight of fecula.

2. The composition according to claim 1, further comprising a cosmetic agent selected from the group consisting of an antioxidant agent, preservative agent, film forming agent, microcrystalline network forming agent, polymeric and copolymeric agent, denaturating agent, consistency agent, moisturizing agent, emollient, and a conditioning agent.

3. The composition according to claim 1, wherein the amount of surfactant is from about 1% to 54% by weight.

4. The composition according to claim 1, wherein the surfactant is selected from the group consisting of: sodium palmate, sodium palm kernelate, sodium stearate, glycerin, cocamidopropylbetaine, decyl-glucose, and sodium tridecyl sulfate.

5. The composition according to claim 1, wherein fecula is selected from the group consisting of: manioc fecula (*Manihot sculenta*), and potato fecula (*Solarium tuberosum*).

6. The composition according to claim 1, wherein the carrier is water.

7. The composition according to claim 1, wherein the carrier is present in an amount from 0.03% to 4% by weight.

8. The composition according to claim 1, wherein the surfactant is present in an amount from 1% to 54% by weight, and the carrier is present in an amount from 0.03% to 4% by weight, and further comprising 8% to 63% by weight of a cosmetic agent.

9. The composition according to claim 1, further comprising up to 8% by weight of at least one or more of an emollient, a consistency agent, film-forming agent, a preservative, an antioxidant, and a denaturating agent.

10. The composition according to claim 1, wherein the surfactant is present in an amount ranging from 1% to 54% by weight and is selected from the group consisting of sodium palmate, sodium palm kernelate, sodium stearate, glycerin, cocaamidopropyl betaine, decyl-glucose, and sodium trideceth sulfate, and combinations thereof.

11. A non-hardenable cosmetic composition for skin cleansing used in the form of a solid composition having malleability and plasticity characteristics when dried or wet, comprising:
   a) from 1% to 54% by weight of at least one surfactant selected from the group consisting of sodium palmate, sodium palm kernelate, sodium stearate, glycerin, cocaamidopropyl betaine, decyl-glucose, and sodium trideceth sulfate, and combinations thereof;
   b) about 36% by weight of fecula;
   c) from 0.03% to 4% by weight of a cosmetically acceptable carrier; and
   d) from 8% to 63% by weight of a cosmetic agent; wherein all amounts refer to the total weight of the composition.

12. A non-hardenable cosmetic composition for skin cleansing used in the form of a solid composition having malleability and plasticity characteristics when dried or wet, comprising:
   a) from 1% to 54% by weight of at least one surfactant;
   b) about 36% by weight of fecula;
   c) from 0.03% to 4% by weight of a cosmetically acceptable carrier; and
   d) from 15% to 63% by weight of a cosmetic agent; wherein all amounts refer to the total weight of the composition.

13. A cosmetic composition according to claim 12, characterized in that the surfactant is selected from the group consisting of anionic, cationic, amphoteric and nonionic surfactants.

14. A cosmetic composition according to claim 13, wherein the surfactant is selected from the group consisting of: sodium palmate, sodium palm kernelate, sodium stearate, glycerin, cocamidopropylbetaine, decyl-glucose, and sodium tridecyl sulfate.

15. A cosmetic composition according to claim 12, wherein fecula is selected from the group consisting of: manioc fecula (*Manihot sculenta*), and potato fecula (*Solarium tuberosum*).

16. A cosmetic composition according to claim 12, wherein the fecula is present in the composition at a ratio of 36% by weight, based on the total weight of the composition.

17. A cosmetic composition according to claim 12, wherein the composition is in the form of a soap.

* * * * *

UNITED STATES PATENT AND TRADEMARK OFFICE
CERTIFICATE OF CORRECTION

PATENT NO. : 8,372,791 B2
APPLICATION NO. : 13/129952
DATED : February 12, 2013
INVENTOR(S) : Brasilino de Carvalho et al.

It is certified that error appears in the above-identified patent and that said Letters Patent is hereby corrected as shown below:

In the Claims:

Column 11,
Line 37, "sodium palm kernelate" should read --sodium palm kemelate--.

Column 12,
Line 40, "sodium palm kernelate" should read --sodium palm kemelate--.

Signed and Sealed this
Fourteenth Day of May, 2013

Teresa Stanek Rea
*Acting Director of the United States Patent and Trademark Office*